US010335775B2

United States Patent
Balaraman et al.

(10) Patent No.: US 10,335,775 B2
(45) Date of Patent: Jul. 2, 2019

(54) MAGNETICALLY SEPARABLE IRON-BASED HETEROGENEOUS CATALYSTS FOR DEHYDROGENATION OF ALCOHOLS AND AMINES

(71) Applicant: Council of Scientific & Industrial Research, New Delhi (IN)

(72) Inventors: Ekambaram Balaraman, Pune (IN); Dinesh Jagadeesan, Pune (IN); Garima Jaiswal, Pune (IN); Sanjay Pandurang Borikar, Pune (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 11 days.

(21) Appl. No.: 15/576,903

(22) PCT Filed: May 26, 2016

(86) PCT No.: PCT/IN2016/050157
§ 371 (c)(1),
(2) Date: Nov. 27, 2017

(87) PCT Pub. No.: WO2016/189553
PCT Pub. Date: Dec. 1, 2016

(65) Prior Publication Data
US 2018/0147568 A1    May 31, 2018

(30) Foreign Application Priority Data
Nov. 12, 2015 (IN) .......................... 3688/DEL/2015

(51) Int. Cl.
*C01B 32/194* (2017.01)
*B01J 27/24* (2006.01)
(Continued)

(52) U.S. Cl.
CPC ............... *B01J 27/24* (2013.01); *B01J 21/18* (2013.01); *B01J 23/745* (2013.01); *B01J 27/22* (2013.01);
(Continued)

(58) Field of Classification Search
CPC .......... B01J 27/22; B01J 27/24; B01J 23/745; C01B 32/194; C07C 45/002;
(Continued)

(56) References Cited

U.S. PATENT DOCUMENTS

| | | | |
|---|---|---|---|
| 9,543,569 B2 * | 1/2017 | Worsley | H01M 4/131 |
| 2012/0012778 A1 * | 1/2012 | Tilley | B82Y 25/00 252/62.55 |

(Continued)

FOREIGN PATENT DOCUMENTS

| | | | | |
|---|---|---|---|---|
| CN | 10-2583336 | * | 7/2012 | ........... C01B 32/192 |
| CN | 10-2974350 | * | 3/2013 | ........... B01J 23/745 |

(Continued)

OTHER PUBLICATIONS

Qiao et al. "Graphene-supported metallic oxide nanometer material as well as preparation method and application thereof" CN102974350 A (Mar. 20, 2013) EPO English Machine Translation. (Year: 2013).*

(Continued)

*Primary Examiner* — Patricia L. Hailey
(74) *Attorney, Agent, or Firm* — Renner Kenner Greive Bobak Taylor & Weber

(57) ABSTRACT

The present invention discloses an iron-based nitrogen doped graphene catalyst, process for preparation thereof and use of said catalyst in oxidant-free catalytic dehydrogenation of alcohols and amines to the corresponding carbonyl compounds, amines and N-heterocylic compounds with extraction of molecular hydrogen as the only by-product.

8 Claims, 3 Drawing Sheets

(51) Int. Cl.

| | | |
|---|---|---|
| *B01J 37/34* | (2006.01) | |
| *B01J 21/18* | (2006.01) | |
| *B01J 23/745* | (2006.01) | |
| *B01J 27/22* | (2006.01) | |
| *B01J 35/00* | (2006.01) | |
| *B01J 37/02* | (2006.01) | |
| *B01J 37/04* | (2006.01) | |
| *B01J 37/08* | (2006.01) | |
| *C07C 45/00* | (2006.01) | |
| *C07C 249/02* | (2006.01) | |
| *C07D 209/02* | (2006.01) | |
| *C07D 215/04* | (2006.01) | |
| *C07D 215/06* | (2006.01) | |
| *C07D 217/02* | (2006.01) | |
| *C07D 219/02* | (2006.01) | |
| *C07D 241/42* | (2006.01) | |
| *C07D 307/48* | (2006.01) | |

(52) U.S. Cl.
CPC ......... *B01J 35/0006* (2013.01); *B01J 35/006* (2013.01); *B01J 35/0013* (2013.01); *B01J 35/0033* (2013.01); *B01J 37/0207* (2013.01); *B01J 37/0213* (2013.01); *B01J 37/04* (2013.01); *B01J 37/086* (2013.01); *B01J 37/343* (2013.01); *C07C 45/002* (2013.01); *C07C 249/02* (2013.01); *C07D 209/02* (2013.01); *C07D 215/04* (2013.01); *C07D 215/06* (2013.01); *C07D 217/02* (2013.01); *C07D 219/02* (2013.01); *C07D 241/42* (2013.01); *C07D 307/48* (2013.01); *C07C 2602/08* (2017.05); *C07C 2602/10* (2017.05)

(58) Field of Classification Search
CPC .............. C07C 249/02; C07C 2602/08; C07C 2602/10; C07D 209/02; C07D 215/04; C07D 215/06; C07D 217/02; C07D 219/02; C07D 241/42; C07D 307/48
USPC ............................... 502/185, 338; 252/62.56
See application file for complete search history.

(56) References Cited

U.S. PATENT DOCUMENTS

| | | | | |
|---|---|---|---|---|
| 2015/0030968 A1* | 1/2015 | Schwab | ................ | H01M 4/96 429/532 |
| 2017/0354953 A1* | 12/2017 | Yu | .......................... | B01J 23/745 |
| 2018/0147568 A1* | 5/2018 | Balaraman | ............ | B01J 37/343 |

FOREIGN PATENT DOCUMENTS

| | | | | | |
|---|---|---|---|---|---|
| CN | 102974350 | A | * | 3/2013 | ............ B01J 23/745 |
| CN | 10-3721736 | | * | 4/2014 | .............. B01J 27/24 |
| CN | 10-4607228 | | * | 5/2015 | .............. B01J 27/24 |
| CN | 10-4984754 | | * | 10/2015 | .............. B01J 27/24 |
| EP | 2687483 | A1 | * | 1/2014 | ............ C01B 31/00 |
| EP | 2792639 | A1 | * | 10/2014 | ............ C25B 11/03 |

OTHER PUBLICATIONS

Josep Albero et al., "Doped graphenes in catalysis." Journal of Molecular Catalysis A: Chemical 408, pp. 296-309. (Year: 2015).*
Ying-zi Chan et al., "Low-temperature synthesized nitrogen-doped iron/iron carbide/partly graphitized carbon as stable cathode catalysts for enhancing bioelectricity generation." Carbon 89, pp. 8-19. (Year: 2015).*
Yanqing Lai, et al., "Fe/Fe3C decorated 3-D porous nitrogen-doped graphene as a cathode material for rechargeable Li-O2 batteries." Electrochinnica Acta 191, pp. 733-742. (Year: 2016).*
Yabin Li et al., "One-step synthesis Fe3N surface-modified Fe3O4 nanoparticles with excellent lithium storage ability." Applied Surface Science 305, pp. 683-688. (Year: 2014).*
Yanlei Tan et al., "N-doped graphene/Fe—Fe3C nano-composite synthesized by a Fe-based metal organic framework and its anode performance in lithium ion batteries." Chemical Engineering Journal 258, pp. 93-100. (Year: 2014).*
Chi-Wen Tsai et al., "Nitrogen-doped graphene nanosheet-supported non-precious iron nitride nanoparticles as an efficient electrocatalyst for oxygen reduction." RSC Advances, 1, pp. 1349-1357. (Year: 2011).*
Zhong-Shuai Wu et al., "3D Nitrogen-Doped Graphene Aerogel-Supported Fe3O4 Nanoparticles as Efficient Electrocatalysts for the Oxygen Reduction Reaction." Journal of the American Chemical Society 134, pp. 9082-9085. (Year: 2012).*

* cited by examiner

MAGNETICALLY SEPARABLE IRON-BASED HETEROGENEOUS CATALYSTS FOR DEHYDROGENATION OF ALCOHOLS AND AMINES

FIELD OF THE INVENTION

The present invention relates to an iron-based nitrogen doped graphene catalyst. More particularly, the present invention relates to a magnetically separable iron nanoparticles supported on nitrogen doped graphene catalyst, process for preparation thereof and use of said catalyst in oxidant-free catalytic dehydrogenation of alcohols and amines to the corresponding carbonyl compounds, amines and N-heterocyclic compounds with extraction of molecular hydrogen as the only by-product.

BACKGROUND AND PRIOR ART OF THE INVENTION

In recent times, earth-abundant, and inexpensive iron-catalysis has become more fascinating and a viable system for environmentally benign reactions. The economical, greener and ample supply of iron salts, coupled with their lack of toxicity, makes them ideal candidates for both the academic and industrial applications. However, search for an efficient catalytic system based on iron-catalysts for sustainable catalysis is extremely rare due to propensity of iron complexes to participate in one electron chemistry as opposed to traditional two electron transformation ubiquitous in the precious second- and third-row transition-metals and to the challenge of working with paramagnetic materials (mostly kinetically labile) and underdeveloped mechanistic studies. Design of a new catalytic system based on earth-abundant, and inexpensive metal catalysts for fundamentally important organic transformations under environmentally-benign conditions is an important paradigm in chemical synthesis.

Iron as a catalyst in chemical synthesis has been experienced renaissance due to not only its abundance and occurrence in various biological systems as essential key element but its activity and selectivity in the synthetic transformations are edge over the state-of-art of precious metal catalysts in certain case. Many iron based catalysed have been proved to be efficient and promising homogeneous catalytic systems by inventing the appropriate non-innocent ligand systems which interfere actively in the catalytic process. Graphene oxide (GO) sheets are emerging as a new class of carbocatalysts. Conventionally, graphite is oxidized to graphene oxide and exfoliated into submicrometer-sized, water-dispersible flakes to produce graphene oxide sheets. The presence of oxygen functional groups on the aromatic scaffold of GO allows these sheets to mediate ionic and nonionic interactions with a wide range of molecules.

Article titled "Efficient and Highly Selective Iron-Catalyzed Reduction of Nitroarenes" by R V Jagadeesh et al. published in *Chem. Commun.*, 2011,47, 10972-10974 reports pyrolysis of iron—phenanthroline complexes supported on carbon leads to highly selective catalysts for the reduction of structurally diverse nitroarenes to anilines in 90-99% yields.

Article titled "Nitrogen-Doped Graphene and Its Iron-Based Composite As Efficient Electrocatalysts for Oxygen Reduction Reaction" by K Parvez et al. published in *ACS Nano*, 2012, 6 (11), pp 9541-9550 reports a cost-effective synthesis of NG by using cyanamide as a nitrogen source and graphene oxide as a precursor, which led to high and controllable nitrogen contents (4.0% to 12.0%) after pyrolysis. NG thermally treated at 900° C. shows a stable methanol crossover effect, high current density, and durability when catalyzing ORR in alkaline solution. Further, iron (Fe) nanoparticles could be incorporated into NG with the aid of Fe (III) chloride in the synthetic process. This allows one to examine the influence of non-noble metals on the electrocatalytic performance.

Article titled "Graphene-supported iron-based nanoparticles encapsulated in nitrogen-doped carbon as a synergistic catalyst for hydrogen evolution and oxygen reduction reactions" by Wang et al. published in *Faraday Discuss.*, 2014, 176, 135-151 reports graphene-supported iron-based nanoparticles encapsulated in a nitrogen-doped carbon (Fe@N—C) hybrid material acts as an efficient HER and ORR catalyst. The hybrid material showed higher electrocatalytic activities than graphene sheets or Fe@N—C alone, which is probably attributed to the synergetic role of nitrogen-doped graphene and Fe@N—C towards the electrocatalytic reactions.

Article titled "Non-precious metal nanoparticles supported on nitrogen-doped graphene as a promising catalyst for oxygen reduction reaction: Synthesis, characterization and electrocatalytic performance" by H Ghanbarlou et al. published in *Journal of Power Sources*, 2015, 273, pp 981-989 reports nitrogen-doped graphene (NG) based non-precious metal catalysts is used as a catalyst for oxygen reduction reaction (ORR). Nanoflower-like NG with designed nitrogen types is directly synthesized using a low temperature solvothermal process and then Fe, Co and Fe—Co nanoparticles are precipitated onto the NG using a modified polyol method.

Article titled "Nitrogen-Doped Graphene-Activated Iron-Oxide-Based Nanocatalysts for Selective Transfer Hydrogenation of Nitroarenes" by RV Jagadeesh et al. published in *ACS Catal.*, 2015, 5 (3), pp 1526-1529 reports Nanoscaled iron oxides on carbon modified with nitrogen-doped graphene (NGr) as an excellent catalysts for the chemoselective transfer hydrogenation of nitroarenes to anilines.

Article titled "Nitrogen-self-doped graphene-based non-precious metal catalyst with superior performance to Pt/C catalyst toward oxygen reduction reaction" by C He et al. published in *J. Mater. Chem. A*, 2014,2, 3231-3236 reports A new, simple and scalable synthesis methodology is invented for an N-self-doped graphene-based non-precious Fe catalyst (Fe—N-graphene) for the oxygen reduction reaction (ORR) both in acidic and alkaline media. The electrochemical characterization shows that this Fe—N-graphene catalyst possesses outstanding electrocatalytic ORR activity.

Article titled "Fe—N—C oxygen reduction catalysts supported on vertically aligned carbon nanotubes" by G C K Liu et 1. published in *Applied Catalysis A: General*, 2008, 347(1), pp 43-49 reports Non-noble metal electrocatalyst (Fe—N—C) for the oxygen reduction reaction (ORR) sputter deposited onto films of vertically aligned carbon nanotubes (VACNT) and tested by the rotating ring disk electrode (RRDE) technique.

Recently, it has been recognized that iron-based dehydrogenation process with liberation of hydrogen gas as the by-product, competes with the state-of-art of precious metal based catalytic systems. Indeed it has a significant development in the conversion of renewable feedstocks into value-added products with complete atom-efficiency.

Dehydrogenation of organic compounds that allow chemical integration of abundant organic substrates (e.g. alkanes and alcohols) into valuable products and find manifold applications in chemical synthesis as well as in energy storage systems. Traditionally, the dehydrogenation of organic compounds has been achieved with the aid of stoichiometric amount of sacrificial oxidants and/or hydrogen acceptors. Recent development of smart catalytic systems allows oxidant-free and acceptorless conditions with the liberation of dihydrogen, an energy carrier. This strategy has been further extended to dehydrogenative cross-couplings and cascade annulations to enable a range of structurally diverse molecules at single operation.

Article titled "Reversible catalytic dehydrogenation of alcohols for energy storage" by P J Bonitatibus et al. published in *PNAS*, 2015, 112 (6), pp 1687-1692 reports reversible acceptorless dehydrogenation of secondary alcohols and diols on iron pincer complexes and reversible oxidative dehydrogenation of primary alcohols/reduction of aldehydes with separate transfer of protons and electrons on iridium complexes.

Article titled "Fe-catalyzed acceptorless dehydrogenation of secondary benzylic alcohols" by H Song et al. published in *ACS Catal.*, 2014, 4 (9), pp 2889-2895 reports an operationally simple, economical, and environmentally benign acceptorless Fe-catalyzed dehydrogenation of various secondary benzylic alcohols to afford the corresponding ketones and $H_2$. A simple in situ mixture of readily available Fe(III) acetylacetonate, 1,10-phenanthroline, and $K_2CO_3$ was identified as an active catalyst for this transformation.

Article titled "Hydrogenation using iron oxide-based nanocatalysts for the synthesis of amines" by R V Jagadeesh et al. published in *Nat Protoc.*, 2015; 10 (4); 548-57 reports the preparation of nanoscale iron oxide-based materials and their use in the catalysis of different hydrogenation reactions. Pyrolysis of a Fe(OAc)$_2$-phenanthroline complex on carbon at 800° C. under argon atmosphere results in the formation of nanoscale $Fe_2O_3$ particles surrounded by nitrogen-doped graphene layers.

Article titled "Well-Defined iron catalysts for the acceptorless reversible dehydrogenation-hydrogenation of alcohols and ketones" by S Chakraborty et al. published in *ACS Catal.*, 2014, 4 (11), pp 3994-4003 reports acceptorless dehydrogenation of alcohols accomplished with well-defined and inexpensive iron-based catalysts supported by a cooperating PNP pincer ligand. Benzylic and aliphatic secondary alcohols were dehydrogenated to the corresponding ketones in good isolated yields upon release of dihydrogen. Primary alcohols were dehydrogenated to esters and lactones, respectively. Mixed primary/secondary diols were oxidized at the secondary alcohol moiety with good chemoselectivity.

Among the various fundamental organic reactions which have industrial application, one such reaction is direct conversion of alcohols to value added products such as carbonyl compounds. Dehydrogenation of alcohols with homogeneous catalysts based on precious metals such as Ru, Jr, and Rh are reported for aerobic oxidation. Metal catalyzed oxidation permit the use of mild, inexpensive, and environmentally benign oxidizing agents, such as $O_2$ or $H_2O_2$. Other mild oxidizing agents used as hydrogen acceptors include included ketones, olefins and amine-N-oxides.

However, in terms of atom economy and the use of hydrogen as fuel, oxidant-free reaction to give carbonyl products via acceptor less alcohol dehydrogenation is desirable.

Catalytic acceptorless dehydrogenation of primary alcohols to esters by soluble Fe(II)-PNP pincer complex is reported in *Science*, 2013, 341, 249.

Traditional approaches to imine synthesis mainly involve condensation of an aldehyde or a ketone with a primary amine, and oxidative condensation of primary amines using strong oxidant. Catalytic oxidative condensation of primary amines using less-toxic oxidants such as oxygen, hydrogen peroxide is well explored. Kobayashi et al. in *Chem. Rev.* 2011, 111, 2626-2704 reports that imines and their derivatives constitute diverse class of organic compounds and have been mostly identified by their profound application in organic synthesis, pharmaceuticals, and agricultural chemicals.

Article titled "Synthesis and Characterization of Iron-Nitrogen-Doped Graphene/Core-Shell Catalysts: Efficient Oxidative Dehydrogenation of N-Heterocycles" by X Cui et al. published in *J. Am. Chem. Soc.*, 2015 July 31, 137 (33), pp 10652-10658 reports synthesis and characterization of iron oxides surrounded by nitrogen-doped-graphene shells immobilized on carbon support (labeled FeOx@NGr—C). Active catalytic materials are obtained in a simple, scalable and two-step method via pyrolysis of iron acetate and phenanthroline and subsequent selective leaching. The optimized FeOx@NGr—C catalyst showed high activity in oxidative dehydrogenations of several N-heterocycles.

However, the reported methods use highly reactive aldehydes, costly metal and high pressure. Also, the water formed during the reported methods leads to back reaction which affects the yield of the desired product. Therefore it is the need to develop an eco-benign and atom-economical process for making value-added imines and/or N-heterocyclic compounds in high yield. Accordingly, the present inventors developed an inexpensive, environment friendly, benign magnetically separable catalyst using earth-abundant elements such as carbon and iron which can be used efficiently in oxidant-free catalytic dehydrogenation of alcohols and amines to corresponding value added product with hydrogen as the only by product.

OBJECTIVE OF THE INVENTION

The main objective of the present invention is to provide a magnetically separable iron nanoparticles supported on nitrogen doped graphene catalyst, wherein said catalyst can be magnetically separated after the reaction and can be reused.

Another objective of the present invention is to provide a process for preparation of magnetically separable iron nanoparticles supported on nitrogen doped graphene catalyst.

Yet another objective of the present invention is to provide magnetically separable iron based catalyst on doped graphene useful for oxidant-free catalytic dehydrogenation of alcohols to value added product such as carbonyl with hydrogen as the only by product.

Still another objective of the invention is to provide magnetically separable iron based catalyst on doped graphene useful for oxidant-free catalytic dehydrogenation of amines to corresponding N-Heterocylic compounds with hydrogen as the only by product.

SUMMARY OF THE INVENTION

The present invention provides a magnetically separable iron nanoparticles supported on nitrogen doped graphene catalyst, wherein the iron nanoparticles has diameter in the range of 10 to 50 nm and iron is present as Iron (III) oxide ($Fe_2O_3$), Iron (II,III) oxide ($Fe_3O_4$), Iron nitride ($Fe_3N$) and Iron carbide ($Fe_3C$, $Fe_7C_3$).

In an embodiment, present invention provides a process for the preparation of iron nanoparticles supported on nitrogen doped graphene catalyst comprising the steps of:
a. sonicating the mixture of Iron(III) acetyl acetone and 1-10-phenanthroline in a ratio ranging between 1 to 3 in solvent for the period in the range of 1 to 2 hrs to obtain a solution;
b. sonicating exfoliated graphene oxide in solvent for the period in the range of 1 to 2 hrs to obtain a solution;
c. mixing the solutions as obtained in step (a) and (b) and further sonicating the mixture for the period in the range of 1 to 2 hrs to obtain a mixture;
d. refluxing the reaction mixture as obtained in step (c) at temperature in the range of 80 to 90° C. for the period in the range of 3 to 5 hrs followed by calcination to afford iron nanoparticles supported on nitrogen doped graphene catalyst.

In an embodiment of the present invention, solvent used in step (a) and (b) is selected from the group consisting of methanol, ethanol, isopropanol, and t-butanol.

In another embodiment of the present invention, said catalyst is useful for dehydrogenation of alcohol or amine and the said process comprising the steps of:
i. refluxing the reaction mixture of alcohol or amine, potassium tert-butoxide and iron based nitrogen doped graphene catalyst in a solvent at temperature in the range of 150 to 160° C. for the period in the range of 30 to 40 hrs to afford the desired products; characterized in that the yield of said desired products is in the range of 50 to 100%.

In yet another embodiment of the present invention, said solvent is selected from the group consisting of octane, mesitylene, xylene, toluene, decane, and dodecane.

In yet another embodiment of the present invention, said alcohol is selected from the group consisting of:

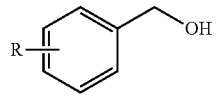

A

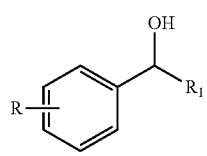

B

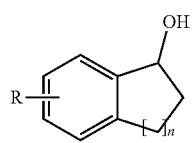

C

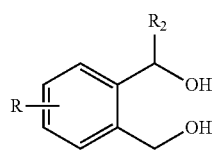

D

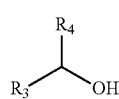

E wherein
R represents mono, di, tri, tetra or penta substituents, wherein each such substituent is independently selected from the group consisting of H, linear or branched alkyl, (un)substituted or substituted cycloalkyl, (un)substituted or substituted aryl, (un)substituted or substituted heteroaryl, alkoxy, phenoxy, (un)substituted or substituted amino, thio, halides, trifluromethyl, nitro, cyano or ester.

$R_1$ represents linear or branched alkyl, (un)substituted or substituted cycloalkyl, (un)substituted or substituted aryl, (un)substituted or substituted heterocyclyl or (un)substituted or substituted heteroaryl;

$R_2$ represents H, linear or branched alkyl,(un)substituted or substituted cycloalkyl, (un)substituted or substituted aryl or (un)substituted or substituted heteroaryl.

$R_3$ represents hydrogen, (un)substituted or substituted alkyl, (un)substituted or substituted aryl, (un)substituted or substituted cycloalkyl or (un)substituted or substituted heteroaryl or $R_4$ is selected independently from hydrogen, (un)substituted or substituted alkyl, (un)substituted or substituted aryl, (un)substituted or substituted cycloalkyl or (un)substituted or substituted heteroaryl;

or $R_3$ and $R_4$ represent together (un)substituted or substituted cyclic compound;

n=1 and 2, which may be further substituted by halides, alkyl (linear and branched), aryl which may be further substituted.

In yet another embodiment of the present invention, said amine is selected from the group consisting of :

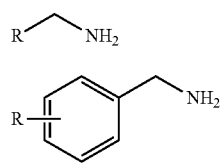

1

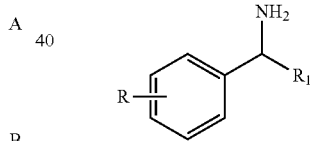

2

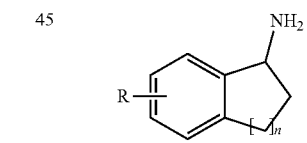

3

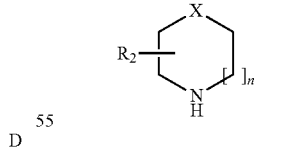

4

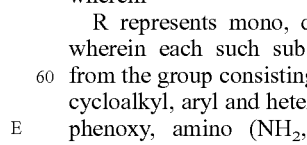

5 wherein
R represents mono, di, tri, tetra or penta substituents, wherein each such substituent is independently selected from the group consisting of H, alkyl (linear and branched), cycloalkyl, aryl and heteroaryl (further substituted), alkoxy, phenoxy, amino ($NH_2$, mono- or di-substituted), thio, halides, trifluromethyl, nitro, cyano, ester.

$R_1$ represents alkyl (linear and branched), cycloalkyl, aryl (which may be further substituted), heterocyclyl, heteroaryl.

$R_2$ represents an aryl fusion with substituents or aryl substituted (which may be further substituted). The substitution may be mono, di, tri or tetra substituents, wherein each such substituent is independently selected from the group consisting of H, alkyl (linear and branched), cycloalkyl, aryl and heteroaryl (further substituted), alkoxy, phenoxy, amino ($NH_2$, mono- or di-substituted), thio, halides, triflurometyl, nitro, cyano, ester;

n=1 and 2, which may be further substituted by halides, alkyl (linear and branched), aryl which may have further substituents.

X is selected from —$CH_2$— or —NH.

In yet another embodiment of the present invention, said desired product is carbonyl compound when alcohol used as reactant.

In yet another embodiment of the present invention, said desired product is imine when said amine is of formula 1.

In yet another embodiment of the present invention, said desired product is N-heterocyclic compound when said amine is cyclic amine of formula 5.

In yet another embodiment of the present invention, said process is carried out under inert atmosphere.

Abbreviations Used
EGO=Exfoliated graphene oxide
NG=Nitrogen doped graphene
FeNG=Iron on Nitrogen doped graphene
RG=Reduced graphene

DETAILED DESCRIPTION OF THE INVENTION

Present invention provides a magnetically separable and reusable iron nanoparticles supported on nitrogen doped graphene catalyst, wherein the magnetisable particles has diameter in the range of 10 to 50 nm.

Iron is present as Iron (III) oxide ($Fe_2O_3$), Iron (II, III) oxide ($Fe_3O_4$), Iron nitride ($Fe_3N$) and Iron carbide ($Fe_3C$, $Fe_7C_3$).

The present invention provides a cost effective, simple process for synthesis of magnetically separable iron nanoparticles supported nitrogen doped graphene catalyst comprising the steps of:

a) sonicating the mixture of Iron(III) acetyl acetone and 1-10-phenanthroline in solvent for the period in the range of 1 to 2 h;

b) sonicating exfoliated graphene oxide in solvent for the period in the range of 1 to 2 h;

c) mixing the solutions of step (i) and (ii) and further sonicating the mixture for the period in the range of 1 to 2 h;

d) refluxing the reaction mixture of step (c) at temperature in the range of 80 to 90° C. for the period in the range of 3 to 5 hrs followed by calcination to afford iron based nitrogen doped graphene catalyst.

Solvent is selected from methanol, ethanol, isopropanol, and t-butanol.

The catalysts may be used in general at upto 250° C. and the reactions may be carried out at any pressure. The novel catalysts can be separated from the reaction mixtures by applying magnetic field.

As prepared graphene (not carbonized in Ar at 800° C. but has been thermally exfoliated at 160° C.)=EGO (Stands for Exfoliated Graphene Oxide).

Graphene+1,10-Phenonthroline ligand carbonized at 800° C. in Ar (without Fe)=NG (Stands for N-doped graphene).

As prepared Fe catalyst after the decomposition of Fe-1, 10-Phenonthroline complex in Ar at 800° C.=FeNG (stands for Fe on N-doped graphene).

RG (stands for EGO heat treated in Ar at 800° C.).

Figure 1:
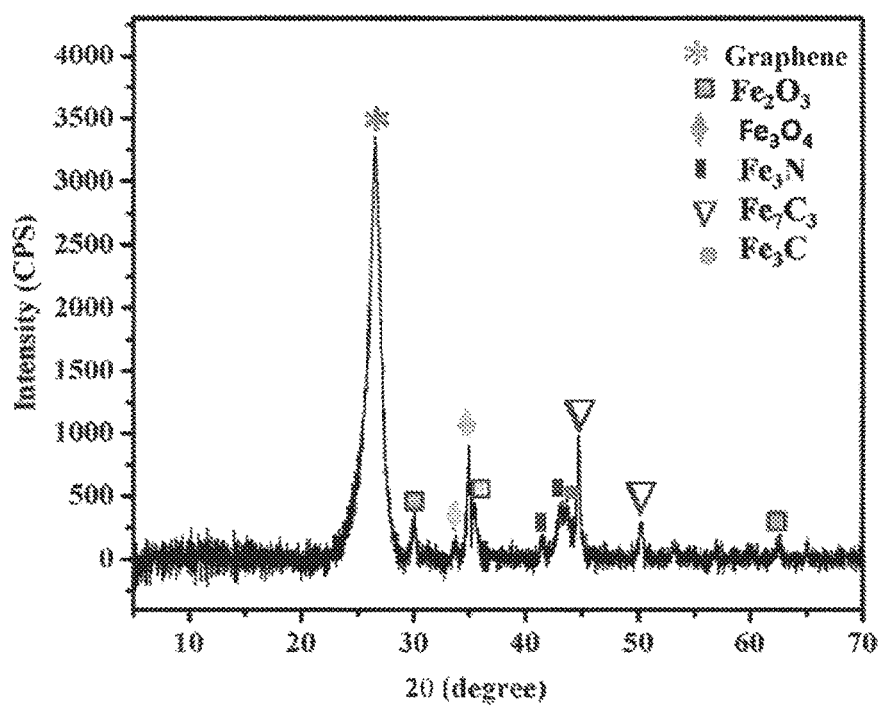
FIG. 1: X-ray Powder Diffraction (XRD) pattern of FeNG material with indices of peaks pattern of β"—$Fe_2O_3$, $Fe_3O_4$, $Fe_7C_3$, $Fe_3N$, $Fe_3C$, and graphene.

The XRD pattern of FeNG sample is presented in FIG. 1, shows diffraction peaks confirming the presence of β"—$Fe_2O_3$, $Fe_3O_4$, $Fe_3N$ and $Fe_7C_3$. A peak at 2θ=26.5 degrees corresponding to (002) lattice plane of graphite is observed. The peak is broad suggesting the carbon support is composed of a few layers of graphene sheets. Formation of $Fe_3N$ is due to the decomposition of Fe-phenonthroline complex on EGO. Formation of $Fe_3O_4$ and β"—$Fe_2O_3$ is usually expected under the reaction conditions in argon atmosphere, where carbon in graphite can act as a reducing agent.

Figure 2:
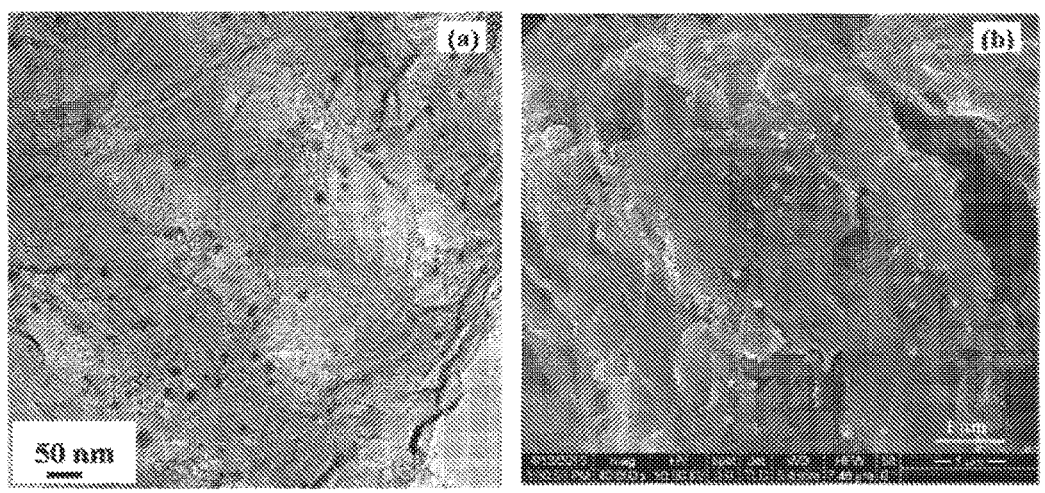
FIG. 2: (a) Transmission electron microscopy (TEM) image of FeNG; Scale bar, 50 nm. (b) Field Emission Scanning Electron Microscope (FESEM) image of FeNG; scale bar, 1 μm.

In FIG. 2, the morphology of the as prepared FeNG catalyst is shown. In FIG. 2a, TEM image of FeNG sample is shown. In the bright field image, one can observe the wrinkles of the thin layers of graphene support as dark lines and Fe-rich nanoparticles as dark spots. It is observed that the nanoparticles are located only on the graphene sheets suggesting a strong chemical interaction between the nanoparticles and the support. The nanoparticles distributed throughout the graphene sheets varied in size from 8 to 50 nm.

In FIG. 2b, the SEM image clearly shows graphene layers with supported Fe-rich nanoparticles. In the dark field FESEM image of FeNG sample, the secondary electrons captured made Fe-rich nanoparticles appear brighter than graphene due to higher electron density of the metal. It is observed that Fe-rich particles are distributed spatially apart and are well supported on the graphene layers.

Figure 3:
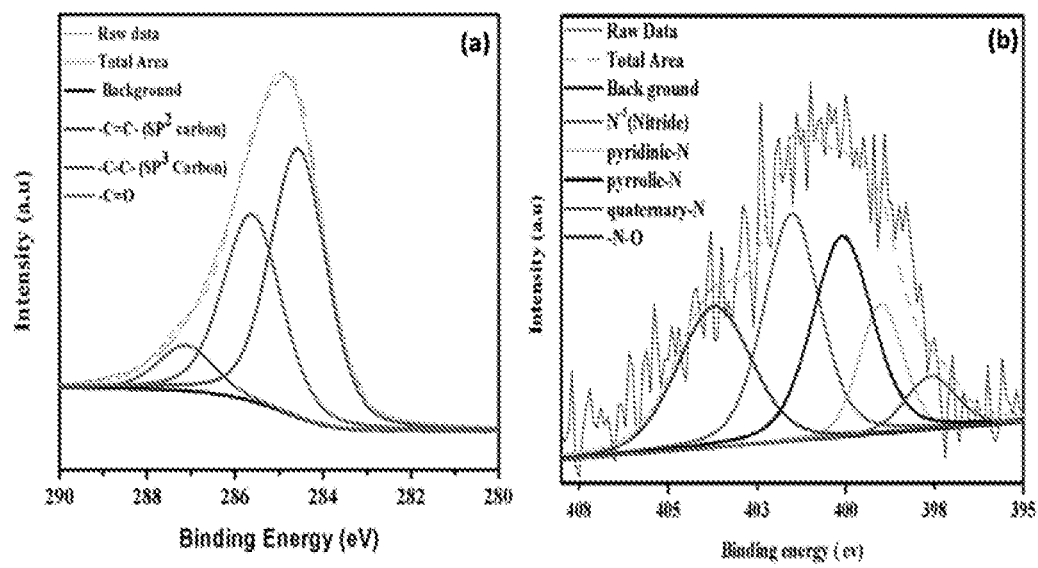
FIG. 3: Deconvoluted X-ray photoelectron spectroscopy (XPS) spectra of FeNG sample: (a) C1s region, (b) N1s region.

The FIG. 3a describes the C1s region of the spectra and FIG. 3b describes the N1s region of the spectra. C1s region of the XPS spectra of the catalyst show four different peaks at 283.5, 284.5, 285.8 and 287.3 eV. The peaks at 283.5 and 284.5 correspond to interstitial carbon in $Fe_7C_3$, and $sp^2$ carbon (—C═C—) groups respectively. The peak at 285.8 eV is ascribed to $sp^3$ carbon such as —C—C— or —C—OH groups. The peak at 287.3 eV is due to carbonyl functional group.

In FIG. 3b, XPS spectra of N1s region of the catalyst has been deconvoluted by fitting the spectra with four sub peaks at 397.5 (N of $Fe_3N$), 399.1 (pyridinic-N/$N_{Pyri.}$), 400.1 (pyrrolic-N/$N_{pyrr.}$), 401.4 eV (quaternary-N/—$NR_4^+$) and 403.6 eV (—N—O). The results are as shown in table 1 below.

TABLE 1

XPS peaks of C1s and N1s in the FeNG

| Peak Position (eV) | Inference |
|---|---|
| C1s Spectra (FIG. 3a) | |
| 284.5 | sp² carbon (—C═C—) |
| 285.8 | sp³ carbon such as —C—C— or —C—OH groups |
| 287.3 | Carbonyl functional group (C═O). |
| N1s Spectra (FIG. 3b) | |
| 397.5 | N of Fe₃N |
| 399.1 | pyridinic-N/$N_{Pyri}$ |
| 400.1 | pyrrolic-N/$N_{Pyrr}$ |
| 401.4 | quaternary-N/$NR_4^+$ |
| 403.6 | —N—O |

Figure 4:
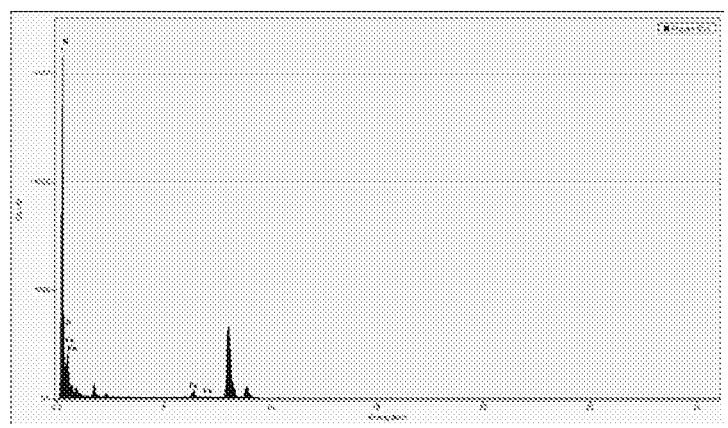
FIG. 4: Energy-dispersive X-ray spectroscopy (EDX), analysis of FeNG.

The EDAX analysis of the catalyst is depicted in FIG. 4. The results of weight percent of different elements in the FeNG is as shown in table 2.

TABLE 2

Weight percent of different elements in the FeNG

| Element | Weight % | Atomic % | Uncert. % | Correction | k-Factor |
|---|---|---|---|---|---|
| C(K) | 76.36 | 83.29 | 0.41 | 0.26 | 3.940 |
| N(K) | 9.23 | 8.64 | 0.17 | 0.26 | 3.826 |
| O(K) | 8.02 | 6.56 | 0.09 | 0.49 | 1.974 |
| Fe(K) | 6.37 | 1.49 | 0.06 | 0.99 | 1.403 |

Figure 5:
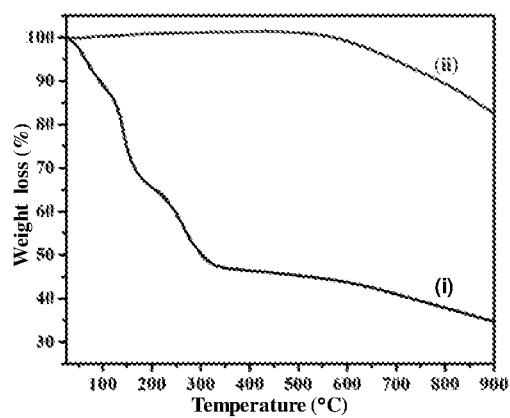
FIG. 5: Thermogravimetric Analysis (TGA) of graphene oxide (black) and FeNG(red).

In FIG. 5 Trace (i) shows TGA curve of fresh graphitic oxide prepared by Hummers method that is used as the starting material to prepare our catalyst. A weight loss at 150° C. is due to loss of physisorbed moisture. The weight loss at 350° C. is characteristic of the loss of oxygen functional groups that are present on the surface of graphitic oxide in the form of epoxide, alcohol and carbonyl groups. In comparison to trace (i), trace (ii) did not show any weight loss at 150 and 350° C. Trace (ii) is graphitic oxide loaded with Fe-phenonthroline complex. The percentage weight loss due to loss of functional groups is not seen due to the presence of relatively heavier Fe element. In addition, Fe is also oxidized to $Fe_2O_3$ and $Fe_3O_4$. (FIG. 4)

Figure 6:
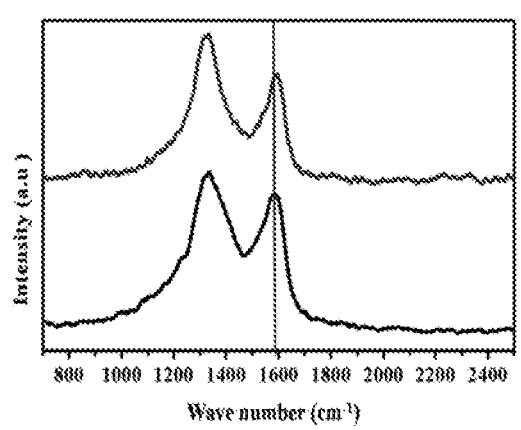
FIG. 6: Raman Spectra of RG (black) and FeNGR (red).
Figure 7:
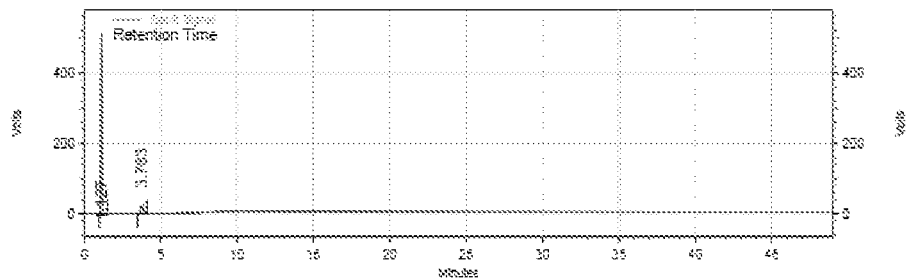
FIG. 7: Qualitative analysis of $H_2$ evolved.

FIG. 6 shows Raman spectra for FeNG and reduced graphene. It mainly shows two peaks. The D band of FeNG located at 1327 cm⁻¹ and 1330 for EGRO. D band is due to the graphitic lattice vibration mode of A1 g symmetry of the sp² carbon lattice and characterizes structural defects or edges that can break the symmetry and selection rule. G band was found at 1595 cm⁻¹ for FeNGR while at 1586 cm⁻¹ for EFGO. G band is due to first-order scattering of the E2 g mode observed for sp² carbon domains, characterizes the highly ordered graphite carbon materials. The relative intensity ratio of D- and G-band ($I_D/I_G$) is a measure of disorder degree. Increased $I_D/I_G$ ratio for FeNGR ($I_D/I_G$=1.36) as compared to EXGO ($I_D/I_G$=1.13) indicating increase in the disorder of graphene after doping of iron nanoparticle on graphene. Peak position G band represents interaction of nanoparticles with graphene. FeNGR shows 9 cm⁻¹ blue shift of G band as compared to EFGO is mainly due to charge transfer from graphene to Iron nanoparticles. However, the electronic role of other phases such as $Fe_3O_4$, $Fe_7C_3$ and $Fe_3N$ are difficult to rule ascertain.

The present invention provides a process for dehydrogenation of alcohol or amine comprises refluxing the reaction mixture of alcohol or amine, potassium tert-butoxide and iron based nitrogen doped graphene catalyst in a solvent at temperature in the range of 150 to 160° C. for the period in the range of 30 to 40 hrs to afford the desired products; characterized in that the yield of said desired products is in the range of 50 to 100%.

Said solvent is selected from octane, mesitylene, xylene, toluene, decane, and dodecane Said process is carried out under inert atmosphere.

Said desired product is carbonyl compound when alcohol used as reactant.

Said alcohol is represented by structure A, B, C, D or E;

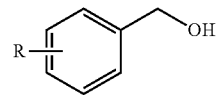

A

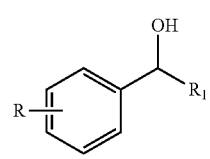

B

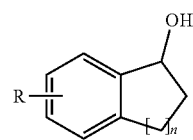

C

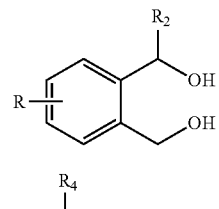

D

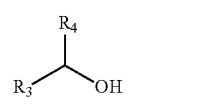

E wherein

R represents mono, di, tri, tetra or penta substituents, wherein each such substituent is independently selected from the group consisting of H, linear or branched alkyl, (un)substituted or substituted cycloalkyl, (un)substituted or substituted aryl, (un)substituted or substituted heteroaryl, alkoxy, phenoxy, (un)substituted or substituted amino, thio, halides, trifluromethyl, nitro, cyano or ester.

$R_1$ represents linear or branched alkyl, (un)substituted or substituted cycloalkyl, (un)substituted or substituted aryl, (un)substituted or substituted heterocyclyl or (un)substituted or substituted heteroaryl;

n=1 and 2, which may be further substituted by halides, alkyl (linear and branched), aryl which may be further substituted.

$R_2$ represents H, linear or branched alkyl,(un)substituted or substituted cycloalkyl, (un)substituted or substituted aryl or (un)substituted or substituted heteroaryl.

Wherein $R_3$ is selected independently from hydrogen, (un)substituted or substituted alkyl, (un)substituted or substituted aryl, (un)substituted or substituted cycloalkyl or (un)substituted or substituted heteroaryl or $R_4$ is selected independently from hydrogen, (un)substituted or substituted alkyl, (un)substituted or substituted aryl, (un)substituted or substituted cycloalkyl or (un)substituted or substituted heteroaryl;

or

R$_3$ and R$_4$ represent together (un)substituted or substituted cyclic compound.

Said amine is represented by formula 1, 2, 3, 4 or 5;

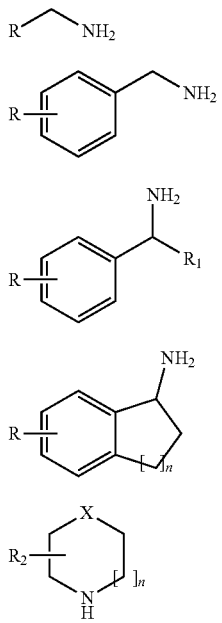

Wherein, R represents mono, di, tri, tetra or penta substituents, wherein each such substituent is independently selected from the group consisting of H, alkyl (linear and branched), cycloalkyl, aryl and heteroaryl (further substituted), alkoxy, phenoxy, amino (NH$_2$, mono- or di-substituted), thio, halides, trifluromethyl, nitro, cyano, ester.

R$_1$ represents alkyl (linear and branched), cycloalkyl, aryl (which may be further substituted), heterocyclyl, heteroaryl.

Wherein, R$_2$ represents an aryl fusion with substituents or aryl substituted (which may be further substituted). The substitution may be mono, di, tri or tetra substituents, wherein each such substituent is independently selected from the group consisting of H, alkyl (linear and branched), cycloalkyl, aryl and heteroaryl (further substituted), alkoxy, phenoxy, amino (NH$_2$, mono- or di-substituted), thio, halides, triflurometyl, nitro, cyano, ester;

n=1 and 2, which may be further substituted by halides, alkyl (linear and branched), aryl which may have further substituents.

X is selected from —CH$_2$— or —NH.

Said desired product is imine when said amine is of formula 1.

Said imine compound is selected from the following:

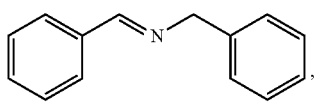

90%* (82% yield)

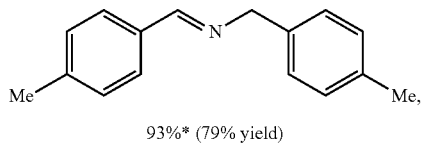

93%* (79% yield)

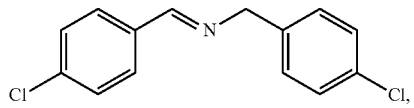

96%* (86% yield)

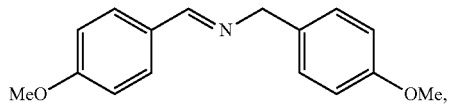

88%* (76% yield)

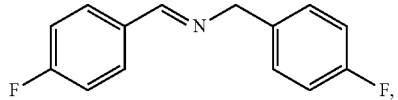

99%* (96% yield)

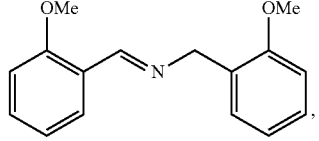

80%* (69% yield)

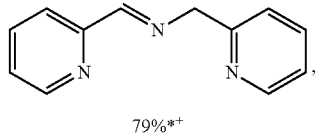

79%*+

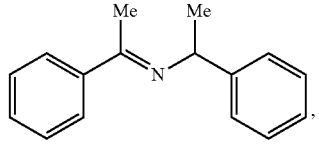

71%*+

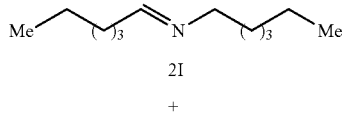

59%* (2l : 3 = 1,1)

Said desired product is N-heterocycle compound when said amine is cyclic amine of formula 5.

The process for the conversion of cyclic amines to N-heterocycle is shown below in Scheme 1:

Scheme: 1
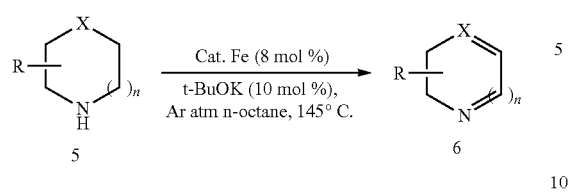
In another preferred embodiment, said N-heterocycle compound is selected from the following:
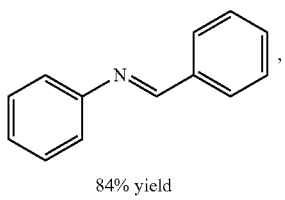
84% yield    5a
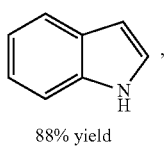
88% yield    5b
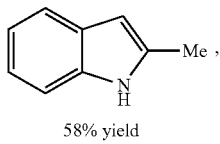
58% yield    5c
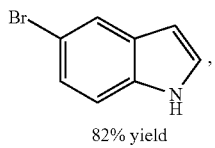
82% yield    5d
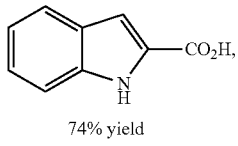
74% yield    5e
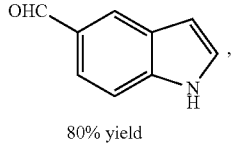
80% yield    5f
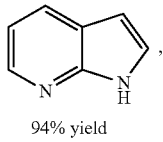
94% yield    5g
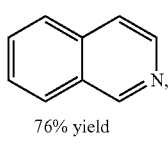
76% yield    5h
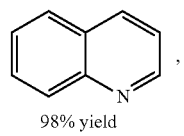
98% yield    5i
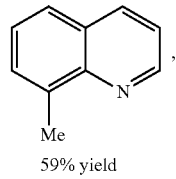
Me
59% yield    5j
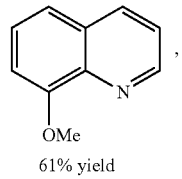
OMe
61% yield    5k
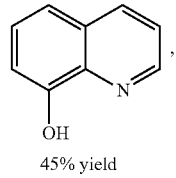
OH
45% yield    5l
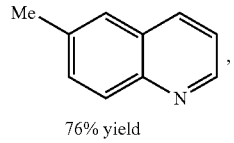
76% yield    5m
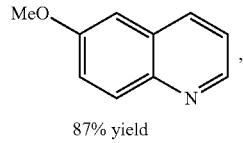
87% yield    5n
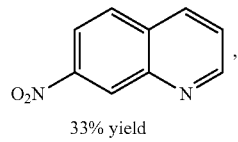
33% yield    5o
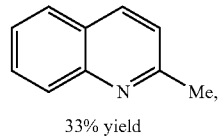
33% yield    5p
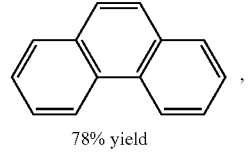
78% yield    5q -continued

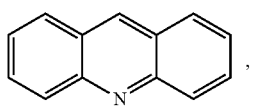

90% yield

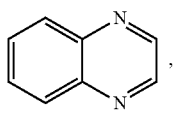

69% yield

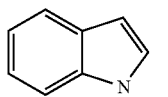

0% yield

Figure 8:
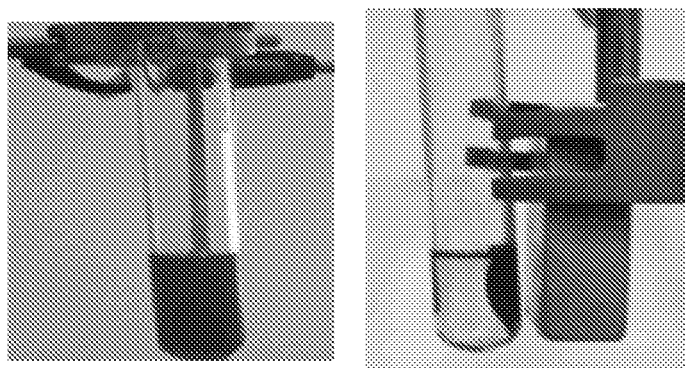
FIG. 8: Separation of the catalyst under strong magnetic field (left: reaction mixture; right: under magnetic field).

The significant advantage of heterogeneous catalysts over soluble homogeneous catalysts is its capability for easy separation and recycling. The iron catalyst is easily separated from the reaction medium under the strong magnetic field, as shown in FIG. 8. The recovered heterogeneous Fe-catalyst was reused for alcohol dehydrogenation, at least, five cycles without considerable loss of the selectivity, although the activity has a slight decay after 5th cycle. The hot filtration test is carried out, and it is observed that no further aldehyde formation took place after the catalyst is filtered off at the conversion of alcohol in 67%. Inductively coupled plasma (ICP) analyzes confirmed that the iron concentration in the filtrate is less than 0.22 ppm. Notably, no aldehyde formation is observed in reaction under complete homogeneous condition.

EXAMPLES

The following examples are given by way of illustration and therefore should not be construed to limit the scope of the invention.

Example 1

Catalyst Preparation

Iron catalyst on nitrogen doped graphene were prepared by mixing Iron(III) acetyl acetone 176 mg (0.5 mmol) and 1-10-phenanthroline 90 mg (0.5 mmol) in 30 mL of ethanol. The mixture was sonicated for 2 hr. In another beaker 560 mg of exfoliated graphene oxide (prepared by hummers method) in 70 mL of ethanol was taken and sonicated for 2 hr. Both the mixtures were mixed together and further sonicated for 2 hr and subsequently refluxed for another 4 hr and the solvent was evaporated using rotary evaporator. Black coloured powder was obtained. It was calcined at 800° C. in argon atmosphere for 4 hr with heating rate of 25° C./min.

Example 2A

Dehydrogenation of Primary Alcohols to Aldehydes

A freshly prepared heterogeneous iron catalyst (10 mol %), $^t$BuOK (8 mol %), primary alcohol (0.5 mmol) and 2 mL of mesitylene were added to a 15 mL Schlenk flask under an atmosphere of argon. The flask was equipped with a reflux condenser and the solution was heated at 155° C. (oil bath temperature) with stirring in an open system under argon for 36 hr (Table 3). The reaction products were analyzed by GC-MS. After cooling to room temperature, m-xylene was added as internal standard to the reaction mixture and the products were quantitatively analyzed by GC.

TABLE 3

Catalytic dehydrogenation of alcohols to aldehyde and molecular hydrogen

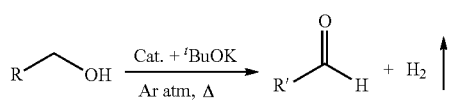

| Entry | Reactant | Product | Conversion[b] | Selectivity[b] |
|---|---|---|---|---|
| 1 | H₃CO-C₆H₄-CH₂OH | H₃CO-C₆H₄-CHO | 98 | 85 (71)[c] |
| 2 | H₃C-C₆H₄-CH₂OH | H₃C-C₆H₄-CHO | 95 | 80 (67)[c] |

TABLE 3-continued

Catalytic dehydrogenation of alcohols to aldehyde and molecular hydrogen $$R\text{—}CH_2OH \xrightarrow[\text{Ar atm, }\Delta]{\text{Cat. + }^tBuOK} R'\text{—}CHO + H_2 \uparrow$$

| Entry | Reactant | Product | Conversion[b] | Selectivity[b] |
|---|---|---|---|---|
| 3 | 4-F-C6H4-CH2OH | 4-F-C6H4-CHO | 55 | 100 |
| 4 | 4-Cl-C6H4-CH2OH | 4-Cl-C6H4-CHO | 99 | 95 (88)[c] |
| 5 | 3,4-(OCH3)2-C6H3-CH2OH | 3,4-(OCH3)2-C6H3-CHO | 60 | 80 |
| 6 | 3-OCH3-C6H4-CH2OH | 3-OCH3-C6H4-CHO | 81 | 90 |
| 7 | 3-Cl-C6H4-CH2OH | 3-Cl-C6H4-CHO | 99 | 100 (92)[c] |
| 8 | 3-OH-C6H4-CH2OH | 3-OH-C6H4-CHO | 60 | 100 |
| 9 | 2,6-(CH3)2-C6H3-CH2OH | 2,6-(CH3)2-C6H3-CHO | 52 | 100 |

TABLE 3-continued

Catalytic dehydrogenation of alcohols to aldehyde and molecular hydrogen

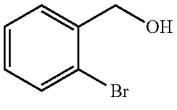

| Entry | Reactant | Product | Conversion[b] | Selectivity[b] |
|---|---|---|---|---|
| 10 | 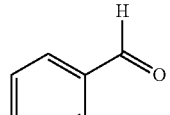 | 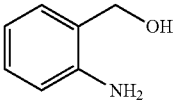 | 71 | 100 (59)[c] |
| 11 | 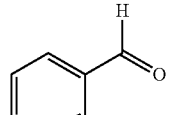 | 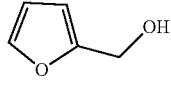 | 67 | 90 |
| 12 | 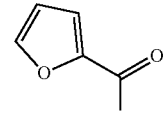 | 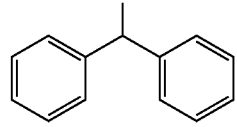 | 50 | 99 |

[b]Conversion and selectivity based on GC of crude reaction mixture using m-xylene as an internal standard.
[c]Yields in parenthesis represent isolated yields.

Example 2B

Dehydrogenation of Sec. Alcohols to Ketones

A freshly prepared heterogeneous iron catalyst (10 mol %), $^t$BuOk (8 mol %), sec.alcohol (0.5 mmol) and 2 mL of mesitylene were added to a 15 mL Schlenk flask under an atmosphere of argon. The flask was equipped with a reflux condenser and the solution was heated at 155° C. with stirring in an open system under argon for 36 hr (Table 4). The reaction products were analyzed by GC-MS. After cooling to room temperature, m-xylene was added as internal standard to the reaction mixture and the products were quantitatively analyzed by GC.

TABLE 4

Catalytic dehydrogenation of sec.alcohols to ketones with liberation of $H_2$

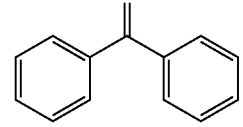

| Entry | Reactant | Product | Conversion[a] | Selectivity[a] |
|---|---|---|---|---|
| 1 | 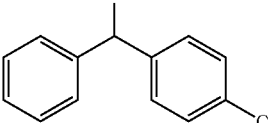 | 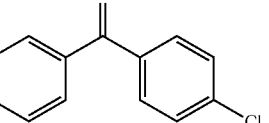 | 99 | 99 (92)[b] |
| 2 | 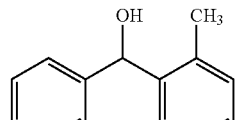 | | 99 | 99 (89)[b] |
| 3 | 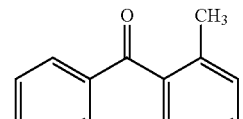 | | 90 | 99 (81)[b] |

TABLE 4-continued

Catalytic dehydrogenation of sec.alcohols to ketones with liberation of H₂

$$\underset{R}{\overset{OH}{\underset{|}{C}}}\underset{R'}{H} \xrightarrow[\text{mesitylene, 155° C.}]{\text{Cat. + }^{t}\text{BuOK (8 mol \%)}} \underset{R}{\overset{O}{\underset{\|}{C}}} R' + H_2 \uparrow$$

| Entry | Reactant | Product | Conversion[a] | Selectivity[a] |
|---|---|---|---|---|
| 4 | 1-phenylethanol | acetophenone | 75 | 93 |
| 5 | 1-(4-methoxyphenyl)ethanol | 4'-methoxyacetophenone | 79 | 99 (68)[b] |
| 6 | 1-(4-methylphenyl)ethanol | 4'-methylacetophenone | 75 | 89 |
| 7 | 1-(4-bromophenyl)ethanol | 4'-bromoacetophenone | 70 | 99 |
| 8 | 1-(4-nitrophenyl)ethanol | 4'-nitroacetophenone | 75 | 99 |
| 9 | 1-(4-methylphenyl)propanol | 4'-methylpropiophenone | 40 | 60 |
| 10 | 1,2,3,4-tetrahydronaphthalen-1-ol | 3,4-dihydronaphthalen-1(2H)-one | 52 | 99 |
| 11 | 5-bromo-1,2,3,4-tetrahydronaphthalen-1-ol | 5-bromo-3,4-dihydronaphthalen-1(2H)-one | 32 | 99 |

TABLE 4-continued

Catalytic dehydrogenation of sec.alcohols to ketones with liberation of $H_2$

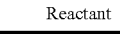

| Entry | Reactant | Product | Conversion[a] | Selectivity[a] |
|---|---|---|---|---|
| 12 | (1-indanol structure) | (1-indanone structure) | 45 | 85 |
| 13 | (1-(naphthalen-2-yl)ethanol structure) | (2-acetonaphthone structure) | 22 | 63 |

[a] Conversion and selectivity based on GC of crude reaction mixture using m-xylene as an internal standard.
[b] Yields in parenthesis represent isolated yields.

Example 3

Dehydrogenation of Diol to Lactone

A freshly prepared heterogeneous iron catalyst (10 mol %), $^t$BuOk (8 mol %), diol (0.5 mmol) and 2 mL of mesitylenewere added to a 15 mL Schlenk flask under an atmosphere of argon. The flask was equipped with a reflux condenser and the solution was heated at 155° C. with stirring in an open system under argon for 36 hr. The reaction products were analyzed by GC-MS. After cooling to room temperature, m-xylene was added as internal standard to the reaction mixture and the products were quantitatively analyzed by GC.

Scheme 1: Catalytic dehydrogenation of diol to lactone and dihydrogen.

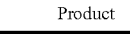

Example 4

Dehydrogenation of Amines to Imines

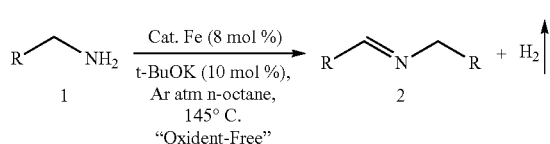

Example 5

Dehydrogenation of Cyclic Amines to N-heterocycles

A freshly prepared heterogeneous iron catalyst (8 mol %), $^t$BuOK (10 mol %), amines 1 (0.5 mmol) and 2 mL of octane were added to a 15 mL Schlenk flask under an atmosphere of argon. The flask was equipped with a reflux condenser and the solution was heated at 145° C. (oil bath temperature) with stirring in an open system under argon for 36 hrs. The reaction products were analyzed by GC and GC-MS. After cooling to room temperature, the reaction mixture was kept under magnetic field and the liquid portion was pipette out. To the solid catalysts ethyl acetate (3×2 mL) was added and repeated the same procedure. Finally the collected organic layer was concentrated under reduced vacuum and the compound was purified through deactivated silica gel chromatography.

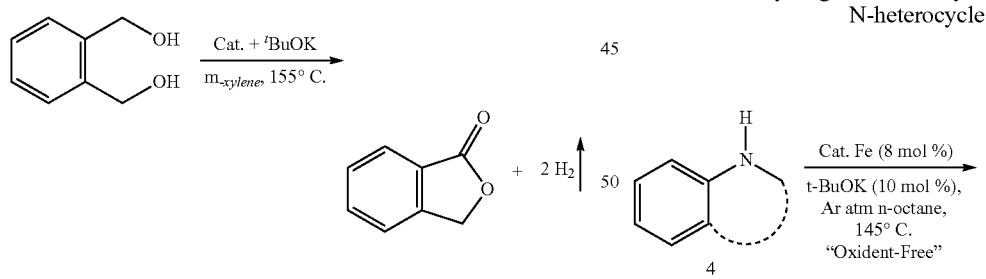

A freshly prepared heterogeneous iron catalyst (8 mol %), $^t$BuOK (10 mol %), cyclic amines 4 (0.5 mmol) and 2 mL of octane were added to a 15 mL Schlenk flask under an atmosphere of argon. The flask was equipped with a reflux condenser and the solution was heated at 145° C. (oil bath temperature) with stirring in an open system under argon for 36 hrs. After cooling to room temperature, the reaction mixture was kept under magnetic field and the liquid portion was pipette out. To the solid catalysts ethyl acetate (3×2 mL) was added and repeated the same procedure. Finally the collected organic layer was concentrated under reduced vacuum and the compound was purified through deactivated silica gel chromatography.

a) (Z)-N-benzylideneaniline

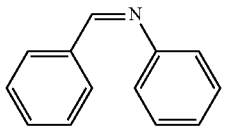 [SMILES: C(=N/c1ccccc1)/c1ccccc1]

$^1$H NMR (500 MHz, CDCl$_3$) δ 4.90 (s, 2H), 7.33-7.35 (m,1H), 7.43-7.44 (m, 4H), 7.48- 7.49 (d, J=4.8 Hz, 3H), 7.87-7.88 (m, 2H), 8.45 (s, 1H); $^{13}$C NMR (125 MHz, CDCl$_3$) δ 64.9, 126.9, 127.0, 128.2, 128.4, 128.5, 130.6, 136.0, 139.2, 161.8.

b) (Z)-4-methyl-N-(4-methylbenzylidene)aniline

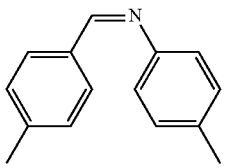 [SMILES: Cc1ccc(/C=N\c2ccc(C)cc2)cc1]

$^1$H NMR (500 MHz, CDCl$_3$) δ 2.35 (s, 3H), 2.39 (s, 3H), 4.78 (s, 2H), 7.15-7.17 (d, J=7.9 Hz, 2H), 7.22-7.28 (d, J=6.4 Hz, 4H), 7.67-7.68 (d, J=7.9 Hz, 2H), 8.35 (s, 1H); $^{13}$C NMR (125 MHz, CDCl$_3$) δ 21.08, 21.4, 64.7, 127.9, 128.2, 129.1, 129.3, 133.6, 136.3, 136.5, 140.9, 161.7 c) (Z)-4-chloro-N-(4-chlorobenzylidene)aniline

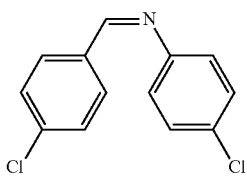 [SMILES: Clc1ccc(/C=N\c2ccc(Cl)cc2)cc1]

$^1$H NMR (200 MHz, CDCl$_3$) δ 4.66 (s, 2H), 7.11-7.28 (m, 6H), 7.49-7.53 (dt, J=6.9 Hz, 1H), 7.69-7.70 (s, 1H), 8.20 (s, 1H); $^{13}$C NMR (25 MHz, CDCl$_3$) δ 64.1, 125.9, 126.6, 127.2, 127.8, 129.9, 129.7, 129.8, 130.8, 134.3, 134.8, 137.6, 141.0, 160.8.

d) (Z)-4-fluoro-N-(4-fluorobenzylidene)aniline

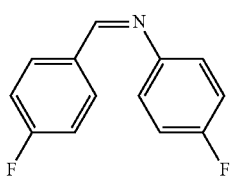 [SMILES: Fc1ccc(/C=N\c2ccc(F)cc2)cc1]

$^1$H NMR (500 MHz, CDCl$_3$) δ 4.78 (s, 2H), 7.04-7.07 (t, J=8.5 Hz, 2H), 7.10-7.14 (t, J=8.5 Hz, 2H), 7.30-7.33 (q, J=5.4 Hz, 2H), 7.78-7.81 (q, J=5.4 Hz, 2H), 8.35 (s, 1H); $^{13}$C NMR (125 MHz, CDCl$_3$) δ 64.0, 115.1, 115.6, 115.7, 129.3, 129.4, 130.0, 130.1, 132.2, 132.3, 134.8, 134.9, 160.4, 160.9, 162.9, 163.3, 165.3 e) (E)-N-benzylideneaniline

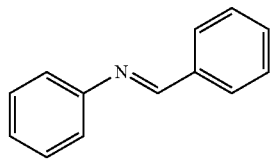 [SMILES: C(=N\c1ccccc1)/c1ccccc1]

$^1$H NMR (500 MHz, CDCl$_3$) δ 7.25-7.29 (m, 3H), 7.42-7.45 (t, J=7.6Hz, 2H), 7.50-7.51 (m, 3H), 7.93-7.95 (dd, J=3.6Hz, 2H), 8.49 (s, 1H); $^{13}$C NMR (125 MHz, CDCl$_3$) δ 120.8, 125.9, 128.7, 128.8, 129.1, 131.3, 136.1, 152.0, 160.4 f) 1H-indole

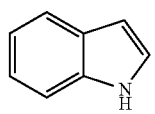

$^1$H NMR (200 MHz, CDCl$_3$) δ 6.62-6.65 (m, 1H), 7.15-7.32 (m, 3H),7.44-7.49 (d, J=8.2 Hz, 1H), 7.70-7.75 (d, J=7.5 Hz, 1H), 8.19 (s, 1H); $^{13}$C NMR (25 MHz, CDCl$_3$) δ 102.6, 110.9, 119.8, 121.9, 124.1, 127.8, 135.7.

g) 2-methyl-1H-indole

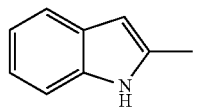

$^1$H NMR (500 MHz, CDCl$_3$) δ 2.46 (s, 3H), 6.29 (s, 1H), 7.15-7.21 (m, 2H), 7.30-7.31(d, J=7.6 Hz, 1H), 7.60-7.11(d, J=7.6 Hz, 1H), 7.75 (s, 1H); $^{13}$C NMR (125 MHz, CDCl$_3$) δ 13.6, 100.2, 110.2, 119.5, 120.8, 128.9, 135.1, 135.9.

h) 5-bromo-1H-indole

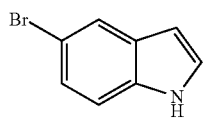

$^1$H NMR (500 MHz, CDCl$_3$) δ 6.52-6.53 (s, 1H), 7.27-7.30 (m, 3H), 7.29 (s, 1H), 8.22 (bs, 1H); $^{13}$C NMR (125 MHz, CDCl$_3$) δ 120.3, 112.4, 113.0, 123.2, 124.8, 125.3, 129.6, 134.4.

i) 1H-indole-2-carboxylic acid

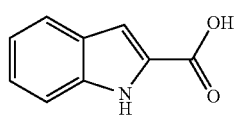

$^1$H NMR (500 MHz, CDCl$_3$) δ 7.18-7.21 (t, J=7.6 Hz, 1H), 7.36-7.40 (m, 2H), 7.46-7.47 (d, J=8.2 Hz, 1H), 7.73-7.75 (d, J=8.2 Hz, 1H), 8.97 (bs, 1H); $^{13}$C NMR (125 MHz, CDCl$_3$) δ 110.8, 111.9, 121.1, 122.9, 126.1, 127.4, 137.3, 166.1.

j) 1H-indole-5-carbaldehyde

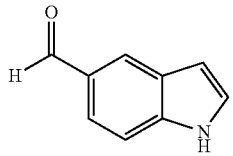 [SMILES: O=Cc1ccc2[nH]ccc2c1]

$^1$H NMR (500 MHz, CDCl$_3$) δ 6.72-6.73 (s, 1H), 7.33-7.34 (t, J=3.0 Hz, 1H), 7.49-7.50 (d, J=8.2 Hz, 1H), 7.78-7.80 (dd, J=8.5 Hz, 1H), 8.20 (s, 1H), 8.95 (bs, 1H), 10.06 (s, 1H); $^{13}$C NMR (125 MHz, CDCl$_3$) δ 104.3, 111.8, 122.2, 126.3, 127.7, 129.6, 139.4, 192.8.

k) 1H-pyrrolo [2.3-b]pyridine

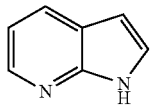

$^1$H NMR (500 MHz, CDCl$_3$) δ 2.97 (bs, 1H), 6.54-6.54 (d, J=3.0 Hz, 1H), 7.11-7.14 (q, J=4.8 Hz, 1H), 7.41-7.41 (q, J=3.3 Hz, 1H), 8.00-8.02 (d, J=7.6Hz, 1H), 8.35-8.35 (d, J=4.5 Hz, 1H), $^{13}$C NMR (125 MHz, CDCl$_3$) δ 110.8, 115.8, 120.7, 125.4, 129.4, 141.9, 148.2.

l) Isoquinoline

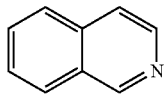

$^1$H NMR (200 MHz, CDCl$_3$) δ 7.34-7.79 (m, 4H), 8.09-8.13 (d, J=7.9 Hz, 2H), 8.90 (s, 1H); $^{13}$C NMR (25 MHz, CDCl$_3$) δ 120.9, 126.4, 127.6, 128.1, 129.2, 129.3, 135.9, 148.0, 150.1.

m) Quinoline

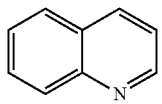

$^1$H NMR (200 MHz, CDCl$_3$) δ 7.63-7.95 (m, 5H), 8.50-8.52 (d, J=5.1Hz, 1H), 9.24 (s, 1H); $^{13}$C NMR (25 MHz, CDCl$_3$) δ 120.4, 126.3, 127.1, 127.5, 128.5, 130.2, 135.6, 142.7, 152.3.

n) 8-methylquinoline

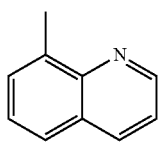

$^1$H NMR (50 MHz, CDCl$_3$) δ 7.33-7.45 (m, 2H), 7.53-7.57 (d, J=6.8Hz, 1H), 7.62-7.66 (d, J=8.0Hz, 2H), 8.08-8.12 (d, J=8.3Hz, 1H), 8.93-8.96 (d, J=1.7Hz, 2H); $^{13}$C NMR (125 MHz, CDCl$_3$) δ 18.0, 120.6, 125.7, 126.1, 128.0, 129.4, 136.1, 136.8, 147.1, 149.0, 149.0 o) 3-methylquinoline

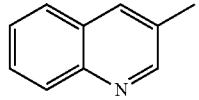

$^1$H NMR (200 MHz, CDCl$_3$) δ 2.37 (s, 3H), 7.37-7.44 (t, J=7.0 Hz, 1H), 7.51-7.64 (m, 2H), 7.51 (s, 1H), 8.01-8.05 (d, J=8.4 Hz, 1H), 8.69 (s, 1H); $^{13}$C NMR (25 MHz, CDCl$_3$) δ 18.6, 126.4, 127.1, 128.3, 129.1, 134.6, 152.3.

p) 6-methylouinoline

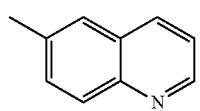

$^1$H NMR (500 MHz, CDCl$_3$) δ 2.47 (s, 3H), 7.26-7.29 (d, J=4.2 Hz, 1H), 7.48-7.49 (m, 2H), 7.97-8.00 (t, J=8.5 Hz, 2H), 7.80-8.81 (dd, J=3.9 Hz, 1H); $^{13}$C NMR (125 MHz, CDCl$_3$) δ 21.3, 120.8, 126.4, 128.1, 128.8, 131.5, 135.1, 136.1, 146.6, 149.2.

q) 6-methoxyquinoline

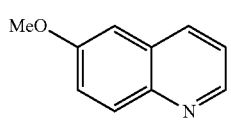

$^1$H NMR (500 MHz, CDCl$_3$) δ 3.92 (s, 3H), 7.05-7.06(d, J=2.7 Hz, 1H), 7.32-7.34 (q, J=4.2 Hz, 1H), 7.35-7.38 (dd, J=9.1 Hz, 1H), 7.99-8.01 (d, J=9.1 Hz, 1H), 8.02-8.04 (d, J=8.2 Hz, 1H), 8.75-8.76 (d, J=4.2 Hz, 1H); $^{13}$C NMR (125 MHz, CDCl$_3$) δ 55.4, 105.1, 121.3, 122.2, 129.3, 130.8, 134.7, 144.4, 147.9, 157.7.

r) 2-methylquinoline

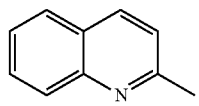

$^1$H NMR (500 MHz, CDCl$_3$) δ 2.70 (s, 1H), 7.18-7.20 (t, J=8.2Hz, 1H), 7.40-7.43 (t, J=7.9Hz, 1H), 7.61-7.64 (t, J=8.5Hz, 1H), 7.68-7.70 (d, J=7.9Hz, 1H), 7.94-7.95 (d, J=8.5Hz, 1H), 7.99-8.01 (d, J=8.5Hz, 1H); $^{13}$C NMR (125 MHz, CDCl$_3$) δ 25.2, 121.8, 124.4, 126.3, 127.3, 128.4, 129.2, 135.9, 147.7, 158.8.

s) benzo[h]quinoline

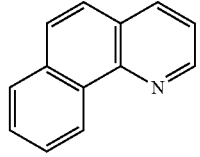 [SMILES: c1ccc2c(c1)ccc1cccnc12]

$^1$H NMR (500 MHz, CDCl$_3$) δ 7.49-7.51 (q, J=4.2 Hz, 1H), 7.65-7.67 (d, J=8.8 Hz, 1H), 7.70-7.73 (td, J=6.7 Hz,

1H), 7.75-7.81 (m, 2H), 7.91-7.92 (d, J=8.2 Hz, 1H), 8.13-8.15 (dd, J=7.9 Hz, 1H), 9.02-9.03 (dd, J=4.5 Hz, 1H), 9.34-9.36 (d, J=7.6 Hz, 1H); $^{13}$C NMR (125 MHz, CDCl$_3$) δ 121.6, 124.3, 125.2, 126.3, 126.9, 127.7, 128.1, 131.4, 133.5, 135.6, 146.5, 146.5, 148.7.

t) Acridine

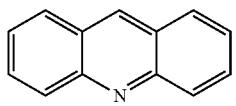 [SMILES: c1ccc2nc3ccccc3cc2c1]

$^1$H NMR (500 MHz, CDCl$_3$) δ 7.49-7.51 (q, J=5.4 Hz, 2H), 7.74-7.78 (m, 2H), 7.94-7.97 (t, J=8.2 Hz, 2H), 8.24-8.25 (t, J=8.8 Hz, 2H), 8.69-8.71 (d, J=9.7 Hz, 1H); $^{13}$C NMR (125 MHz, CDCl$_3$) δ 125.6, 126.5, 128.1, 129.3, 130.1, 149.0.

u) Ouinoxaline

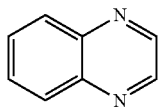

$^1$H NMR (500 MHz, CDCl$_3$) δ 7.41(s, 2H), 7.78-7.81 (m, 2H), 8.51-8.54 (m, 2H); $^{13}$C NMR (125 MHz, CDCl$_3$) δ 128.8, 129.3, 142.2, 144.3.

Example 6

Reusability and Heterogeneity

The significant advantage of heterogeneous catalysts over soluble homogeneous catalysts is its capability for easy separation and recycling. The iron catalyst was easily separated from the reaction medium under the strong magnetic field, as shown in FIG. 8. The recovered heterogeneous Fe-catalyst was reused for alcohol dehydrogenation, at least, five cycles without considerable loss of the. The hot filtration test was carried out, and it was observed that no further aldehyde formation took place after the catalyst was filtered at the conversion of alcohol in 67%. Inductively coupled plasma (ICP) analyzes confirmed that the iron concentration in the filtrate was less than 0.22 ppm. Notably, no aldehyde formation was observed in reaction under complete homogeneous condition All these results clearly demonstrate that the present Fe-catalysis is truly heterogeneous in nature.

ADVANTAGES OF THE INVENTION

Novel catalyst FeNG heterogeneous catalyst which uses commercially inexpensive, earth-abundant elements such as carbon and Iron unlike several organometallic complexes containing precious metals such as Ru, Ir, and Rh.
Employs a simpler method of preparation of catalyst.
The catalyst does not require any hydrogen acceptor unlike its heterogeneous counterparts based on Ru, Ag, Au and Re.
The catalyst is magnetically separable.
The process is carried out under inert atmosphere.

We claim:
1. An iron based nitrogen doped graphene catalyst comprising magnetically separable iron nanoparticles supported on a nitrogen doped graphene catalyst, wherein the iron nanoparticles have a diameter in the range of 10 to 50 nm and iron is present as Iron (III) oxide (Fe$_2$O$_3$), Iron (II/III) oxide (Fe$_3$O$_4$), Iron nitride (Fe$_3$N) and Iron carbide (Fe$_3$C, Fe$_7$C$_3$).

2. A process for dehydrogenation of alcohol or amine comprising the steps of:
 i. refluxing a reaction mixture of alcohol or amine, potassium tert-butoxide and an iron based nitrogen doped graphene catalyst in a solvent at a temperature in the range of 150 to 160° C. for the period in the range of 30 to 40 hrs to afford the desired products; characterized in that the yield of said desired products is in the range of 50 to 100%, wherein the iron based nitrogen doped graphene catalyst includes magnetically separable iron nanoparticles supported on a nitrogen doped graphene catalyst, wherein the iron nanoparticles have a diameter in the range of 10 to 50 nm and iron is present as Iron (III) oxide (Fe$_2$O$_3$), Iron (II/III) oxide (Fe$_3$O$_4$), Iron nitride (Fe$_3$N) and Iron carbide (Fe$_3$C Fe$_7$C$_3$).

3. The process as claimed in claim 2, wherein said solvent is selected from the group consisting of octane, mesitylene, xylene, toluene, decane, and dodecane.

4. The process as claimed in claim 2, wherein said alcohol is selected from the group consisting of:

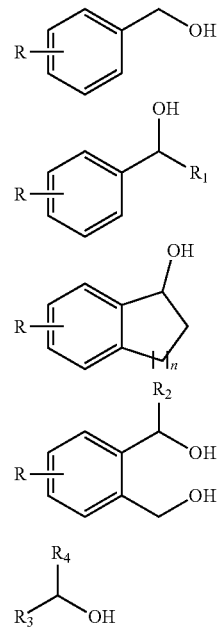

E wherein
R represents mono, di, tri, tetra or penta substituents, wherein each such substituent is independently selected from the group consisting of H, linear or branched alkyl, (un)substituted or substituted cycloalkyl, (un)substituted or substituted aryl, (un)substituted or substituted heteroaryl, alkoxy, phenoxy, (un)substituted or substituted amino, thio, halides, trifluromethyl, nitro, cyano or ester;
Ri represents linear or branched alkyl, (un)substiluted or substituted cycloalkyl, (un)substituled or substituted aryl, (un)substituted or substituted heterocyclyl or (un)substituted or substituted heteroaryl;

R₂ represents H, linear or branched alkyl, (un)substituted or substituted cycloalkyl, (un)substituted or substituted aryl or (un)substituted or substituted heteroaryl, R₃ represents hydrogen, (un)substituted or substituted alkyl, (un)substituted or substituted aryl, (un)substituted or substituted cycloalkyl or (un)substituted or substituted heteroaryl or R₄ is selected independently from hydrogen, (un)substituted or substituted alkyl, (un)substituted or substituted aryl, (un)substituted or substituted cycloalkyl or (un)substituted or substituted heteroaryl;

or R₃ and R₄ represent together (un)substdtuted or substituted cyclic compound; n=1 and 2, which may be further substituted by halides, alkyl (linear and branched), aryl which may be further substituted.

5. The process as claimed in claim 2, wherein said amine is selected from the group consisting of:

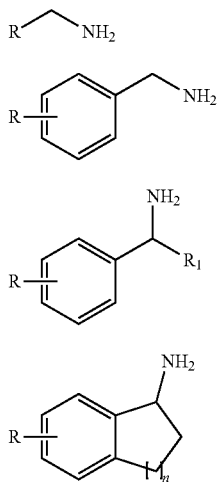

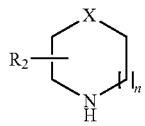

wherein
R represents mono, di, tri, tetra or penta substituents, wherein each such substituent is independently selected from the group consisting of H, alkyl (linear and branched), cycloalkyl, aryl and heteroaryl (further substituted), alkoxy, phenoxy, amino (NH₂, mono- or di-substituted), thio, halides, trifluromethyl, nitro, cyano, ester, R₁ represents alkyl (linear and branched), cycloalkyl, aryl (which may be further substituted), heterocyclyl, heteroaryl;

R₂ represents an aryl fusion with substituents or aryl substituted (which may be further substituted), The substitution may be mono, di, tri or tetra substituents, wherein each such substituent is independently selected from the group consisting of H, alkyl (linear and branched), cycloalkyl, aryl and heteroaryl (further substituted), alkoxy, phenoxy, amino (NH₂, mono- or di-substituted), thio, halides, trifluromelyl, nitro, cyano, ester; n=1 and 2, which may be further substituted by halides, alkyl (linear and branched), aryl which may have further substituents, X is selected from —CH₂— or —NH.

6. The process as claimed in claim 2, wherein said desired product is carbonyl compound when alcohol used as reactant.

7. The process as claimed in claim 2, wherein said desired product is imine when said amine is of formula 1.

8. The process as claimed in claim 2, wherein said desired product is N-hetcrocyclic compound when said amine is cyclic amine of formula 5.

* * * * *